(12) United States Patent
Maligres et al.

(10) Patent No.: US 6,469,172 B2
(45) Date of Patent: Oct. 22, 2002

(54) PROCESS FOR THE PREPARATION OF CHEMICAL COMPOUNDS

(75) Inventors: Peter E. Maligres, Fanwood; Jaemoon Lee, Edison, both of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/799,440

(22) Filed: Mar. 5, 2001

(65) Prior Publication Data

US 2001/0051727 A1 Dec. 13, 2001

Related U.S. Application Data

(60) Provisional application No. 60/187,816, filed on Mar. 8, 2000.

(51) Int. Cl.[7] .............................................. C07D 401/06
(52) U.S. Cl. ........................................ 546/193; 546/194
(58) Field of Search ................................. 546/194, 193

(56) References Cited

U.S. PATENT DOCUMENTS 5,948,792 A    9/1999   Tsuchiya et al.

FOREIGN PATENT DOCUMENTS

WO     099 11620   * 11/1999   .................. 546/194

OTHER PUBLICATIONS

Chem. Abs. vol. 130 No. 223170, Lowe, "Preparation of branched alkoxy–substituted 2–aminopyridines as NOS inhibitors" (1999).*

* cited by examiner

Primary Examiner—Alan L. Rotman
Assistant Examiner—Raymond Covington
(74) Attorney, Agent, or Firm—Mollie M. Yang; David L. Rose

(57) ABSTRACT

An improved and efficient synthesis for the preparation of 2-amino-6-[(4-aminopiperidin-1-yl]methyl]pyridine, an intermediate compound in the preparation of muscarinic M3 receptor antagonists, includes as a final step the removal of trimethylacetyl and an amino protecting group from 2-trimethylacetyl-amino-6-[(4-protected aminopiperidin-1-yl)methyl]pyridine.

9 Claims, No Drawings

PROCESS FOR THE PREPARATION OF CHEMICAL COMPOUNDS

CROSS-REFERENCE TO RELATED APPLICATIONS

This application is a non-provisional application related to U.S. Provisional Application Ser. No. 60/187,816 filed on Mar. 8, 2000 priority of which is claimed hereunder.

BACKGROUND OF THE INVENTION

U.S. Pat. No. 5,948,792 discloses fluorine-containing 1,4-disubstituted piperidine derivatives. These compounds are muscarinic M3 receptor antagonists useful for the treatment or prophylaxis of respiratory diseases such as chronic obstructive pulmonary diseases, chronic bronchitis, asthma and rhinitis; digestive diseases such as irritable bowel syndrome, convulsive colitis, diverticulitis and pain accompanying contraction of smooth muscles of the digestive system; urinary disorders like urinary incontinence and frequency in neurogenic pollakiuria, neurogenic bladder, nocturnal enuresis, unstable bladder, cystospasm and chronic cystisis; and motion sickness.

(2R)-N-[1-(6-aminopyridin-2-ylmethyl)piperidin-4-yl]-2-[(1R)-3,3-difluorocyclopentyl]-2-hydroxy-2-phenylacetamide (A) is a potent and selective M3 receptor antagonist; its preparation from (2R)-2-[(1R)-3,3-difluorocyclopentyl]-2-hydroxyphenylacetic acid and 2-amino-6-[(4-aminopiperidin-1-yl)methyl]pyridine is described in U.S. Pat. No. 5,948,792.

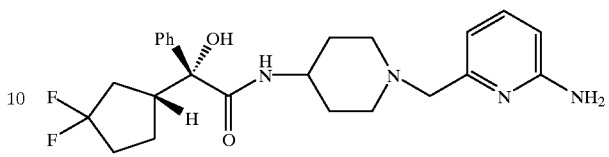

(A)

The synthesis of 2-amino-6-[(4-aminopiperidin-1-yl)methyl]pyridine (I) described in U.S. Pat. No. 5,948,792 is summarized below:

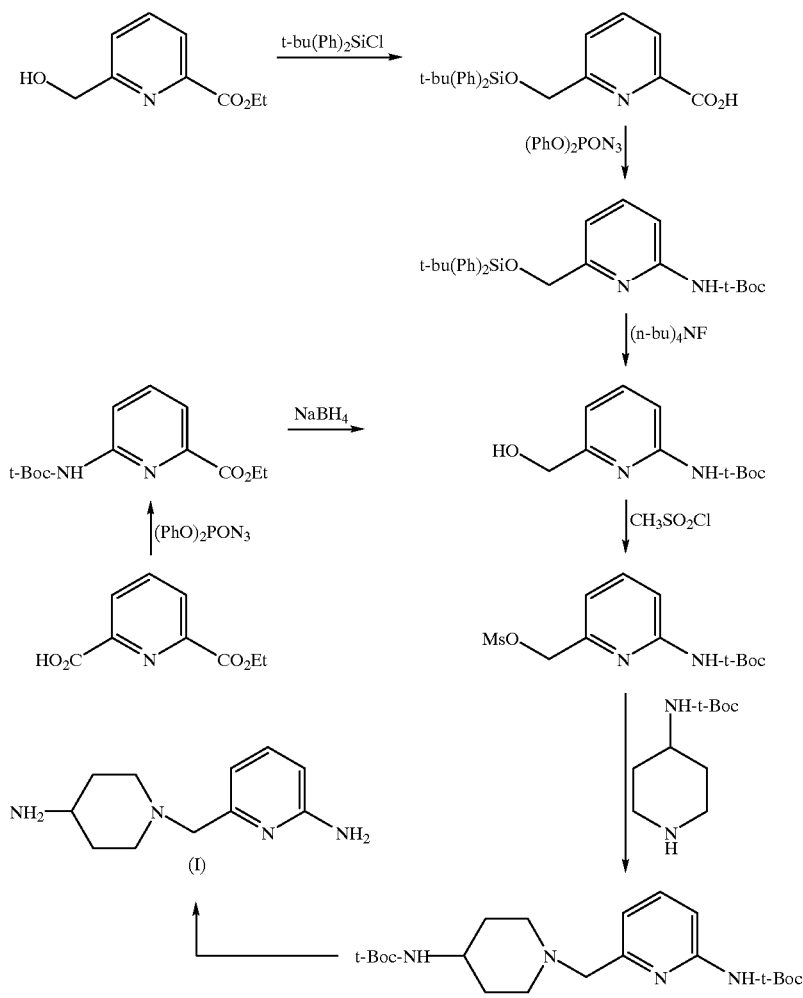

The previous synthetic routes to compound (I) involved a cryogenic reaction, large reaction volumes, reactions under high pressure, the use of relatively expensive reagents and provided compound (I) containing problematic impurities. Thus there remains a need for an improved synthetic route to compound (I) that is amenable to large scale production without having to resort to relatively inaccessible reagents, extreme temperatures and pressures or toxic metals.

SUMMARY OF THE INVENTION

The present invention provides an improved process for the preparation of 2-amino-6-[(4-aminopiperidin-1-yl)methyl]pyridine acid addition salts using commercially available starting materials, intermediates in the process, as well as an improved process for the preparation of the M3 antagonistic compound of formula (A).

DETAILED DESCRIPTION OF THE INVENTION

In one aspect the present invention provides a process for the preparation of 2-amino-6-[(4-aminopiperidin-1-yl)methyl]pyridine of formula (I) acid addition salt:

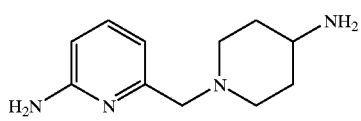

which comprises the steps of:

a) treating 2-(trimethylacetylamino)-6-[(4-protected aminopiperidin-1-yl)methyl]pyridine with a mineral acid or a strong organic acid; and b) isolating the acid addition salt of 2-amino-6-[(4-aminopiperidin-1-yl)methyl]pyridine.

In another aspect, the process further comprises the step of providing 2-(trimethylacetylamino)-6-[(4-protected aminopiperidin-1-yl)methyl]pyridine by reacting 2-(trimethylacetylamino)-6-formylpyridine with 4-protected aminopiperidine or an acid addition salt thereof, in the presence of a reducing agent.

In a further aspect, the process comprises the additional step of providing 2-(trimethylacetylamino)-6-formylpyridine by treating 2-(trimethylacetylamino)-6-bromopyridine with a metallating agent followed by a formamide of the formula $HC(O)NR^1R^2$ wherein $R^1$ and $R^2$ are independently selected from $C_{1-5}$alkyl and phenyl.

In a further aspect the process comprises the additional step of providing 2-(trimethylacetylamino)-6-bromopyridine by reaction 2-amino-6-bromopyridine with an acylating agent derived from trimethylacetic acid.

The above reactions are depicted in the following Scheme 1 starting from 2-amino-6-bromopyridine:

Scheme 1

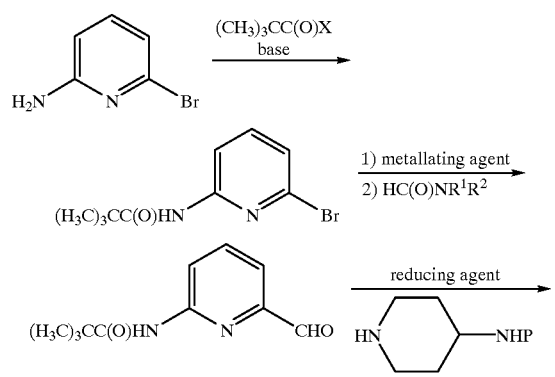

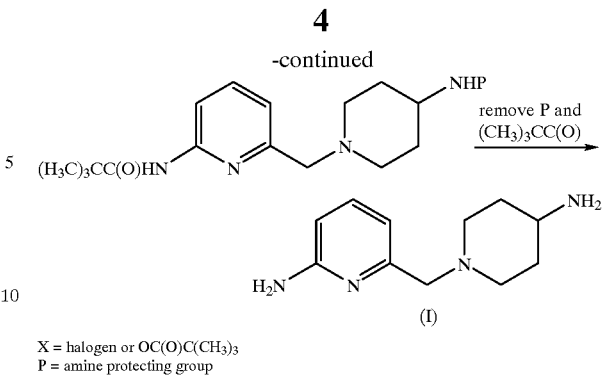

X = halogen or $OC(O)C(CH_3)_3$
P = amine protecting group

In the first step, commercially available 2-amino-6-bromopyridine is treated with an acylating agent derived from trimethylacetic acid such as trimethylacetyl chloride or trimethylacetic anhydride, preferably trimethylacetyl chloride, in the presence of a base. Suitable base includes tertiary amines such as triethylamine, tributyl amine, diisopropylethylamine, pyridine, picoline, lutidine, collidine, imidazole and the like. The reaction is carried out in an aprotic solvent such as chlorinated hydrocarbons such as dichloromethane, dichloroethane or dichlorobenzene; hydrocarbons such as toluene, xylene, cyclohexane, hexane or heptane; ethers such as methyl t-butyl ether, dibutyl ether, tetrahydrofuran or the glymes; esters such as ethyl acetate, isopropyl acetate or butyl acetate; or other polar aprotic solvents such as acetonitrile, dimethylformamide, N-methylpyrrolidinone or dimethylsulfoxide. Glymes as used herein include ethylene glycol dimethyl ether (dimethoxyethane), diethylene glycol dimethyl ether, triethylene glycol dimethyl ether, and the like. The reaction is conducted at a temperature of between about 0° C. to about 50° C., preferably from about 20 to about 50° C.

In the second step, 2-(trimethylacetylamino)-6-bromopyridine is treated with a metallating agent followed by a formamide of the formula $HC(O)NR^1R^2$ wherein $R^1$ and $R^2$ are independently selected from $C_{1-5}$alkyl and phenyl to provide 2-(trimethylacetyl)-6-formylpyridine. Suitable metallating agent are for example, Grignard reagent such as cyclohexylmagnesium chloride, isopropylmagesium chloride, and the like; alkyllithium such as n-butyllithium; dialkyl magnesium compounds such as dibutylmagnesium or diisopropylmagnesium; or mixtures of an alkyl lithium with a Grignard reagent, a dialkylmagnesium, or a magnesium halide. The preferred metallating agent is isopropylmagnesium chloride. The reaction is carried out in an organic solvent such as hydrocarbons such as toluene, xylene, cyclohexane, hexane or heptane; ethers such as tetrahydrofuran, diethyl ether, dibutyl ether, or the glymes. The reaction is carried out at temperature of between about 0–25° C., preferably from about 0 to about 20° C., and optionally in the presence of a complexing agent such as tetramethyl ethylenediamine. The metallation reaction is typically complete within about 24 hours. The metallated species is then converted to the aldehyde using a formamide such as dimethylformamide or N-methyl N-phenylformamide.

In the third step, reductive amination of 2-(trimethylacetyl)-6-formylpyridine is accomplished using a 4-protected aminopiperidine, preferably as a carboxylic acid salt such as the acetate or formate salt, in the presence of a reducing agent such as sodium triacetoxyborohydride, sodium borohydride, sodium cyanoborohydride, borane and its adducts, formic acid, or catalytic hydrogenation. The reaction is carried out in a solvent such as dimethylformamide, acetonitrile, ethers such as tetrahydrofuran, dibutyl ether, tetrahydropyran or the glymes; esters such as ethyl acetate, methyl acetate, isopropyl acetate or butyl acetate; alcohols such as methanol, ethanol or isopropanol, propanol, butanol or methoxyethanol; or other polar aprotic solvents such as N-methylpyrrolidinone or dimethylsulfoxide. The reaction is carried out at a temperature of between about −40° C. to about room temperature, and conveniently may be carried out at ambient temperature. The amino protecting group for 4-aminopiperidine may be a conventional amino protecting group, and preferably one that can be easily removed concurrently with the trimethylacetyl group, such as lower alkanoyl, for example acetyl, and alkoxycarbonyl, for example t-butoxy-carbonyl. The 4-(protected amino) piperidine is preferably used in the presence of a lower alkanoic acid such as acetic or formic acid bound to the piperidine. In a preferred embodiment, the 4-(protected amino)piperidine is N-(4-piperidinyl)-acetamide acetic acid salt; the reductive amination product, 2-(trimethylacetylamino)-6-[(4-acetylamino)-1-piperidinyl) methyl]pyridine, is a crystalline material which can be easily purified and isolated.

In the fourth step, the amino protecting group and the trimethylacetyl group of 2-(trimethylacetylamino)-6-[(4-protected amino)-1-piperidinyl)methyl]-pyridine are removed. The specific reagent and conditions used will depend on the protecting group. Preferably, the amino protecting group is one that can be removed using the reagent and under conditions suitable for removal of the trimethylacetyl group. Conveniently, the amino group may be protected as the acetamide, which may be deprotected by heating aqueous mineral acid such as HCl, HBr or sulfuric acid in an alcohol such as methanol, ethanol, propanol or isopropanol to reflux. Strong organic acid such as sulfonic acids such as methanesulfonic or toluenesulfonic acid may be used in place of the mineral acid. The amino group may also be protected as the carbamate, in which case, deprotection is performed by treatment with mineral acid such as HCl, HBr or sulfuric acid as well as strong organic acids such as the sulfonic acids ie methanesulfonic acid and toluenesulfonic acid, with or without water, in an alcohol such as methanol, ethanol, propanol or isopropanol as well as any solvent that does not compete significantly with the substrate in the deprotection.

The product of the deprotection step may be purified and isolated using conventional separation techniques such as crystallization or resin chromatography.

In another aspect of the present invention there are provided the following novel compounds: 2-(trimethylacetylamino)-6-bromopyridine; 2-(trimethylacetylamino)-6-formylpyridine; and 2-(trimethylacetylamino)-6-[(4-protected amino-piperidin-1-yl)methyl]pyridine.

In yet another aspect the present invention provides a process for the preparation of the M3 antagonist compound (2R)-N-[1-(6-aminopyridin-2-ylmethyl)-piperidin-4-yl]-2-[(1R)-3,3-difluorocyclopentyl]-2-hydroxy-2-phenylacetamide (formula A) or a pharmaceutically acceptable thereof, which comprises the steps of:

a) treating 2-(trimethylacetylamino)-6-[(4-protected aminopiperidin-1-yl)methyl]pyridine with a mineral acid or a strong organic acid;

b) isolating the acid addition salt of 2-amino-6-[(4-aminopiperidin-1-yl)methyl]pyridine;

c) reacting the product of step b) with an acid of the formula (B)

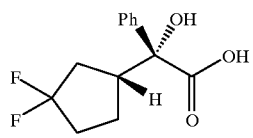

an acylating agent thereof;

d) optionally converting the product of step c) into a corresponding pharmaceutically acceptable salt.

The first two steps in the above process have been previously described in detail. The coupling of the acid of formula (B) and the amine of formula (I) maybe carried out under conventional amide formation conditions. Thus, the reaction may be carried out in the presence of coupling agents such as a carbodiimide (e.g., 1-ethyl -3-(3-dimethylaminopropyl)carbodiimide) and hydroxybenzotriazole. The acid may also be converted into an acylating equivalent, such as the corresponding acid chloride, and reacted with the amine compound in the presence of a base such as secondary and tertiary amines.

As compound of formula (A) contains basic nitrogen atoms, it may be converted to pharmaceutically acceptable acid addition salts by treatment with an appropriate acid. Suitable acids include inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

In another aspect, the process for the preparation of compound of formula (A) further comprises the step of providing 2-(trimethylacetylamino)-6-[(4-protected aminopiperidin-1-yl)methyl]pyridine by reacting 2-(trimethylacetylamino)-6-formylpyridine with 4-protected aminopiperidine or an acid addition salt thereof, in the presence of a reducing agent.

In a further aspect, the process for the preparation of compound of formula (A) comprises the additional step of providing 2-(trimethylacetylamino)-6-formylpyridine by treating 2-(trimethylacetylamino)-6-bromopyridine with a metallating agent followed by a formamide of the formula $HC(O)NR^1R^2$ wherein $R^1$ and $R^2$ are independently selected from $C_{1-5}$ alkyl and phenyl.

In a further aspect the process for the preparation of compound of formula (A) comprises the additional step of providing 2-(trimethylacetylamino)-6-bromopyridine by reacting 2-amino-6-bromopyridine with an acylating agent derived from trimethylacetic acid.

The various additional steps for the preparation of 2-(trimethylacetylamino)-6-bromopyridine have already been described in detail hereinabove.

The following examples are provided to illustrate the invention and are not to be construed as limiting the invention in any manner.

EXAMPLE 1

Preparation of 2-amino-6-[(4-aminopiperidin-1-yl) methyl]pyridine trihydrochloride salt—Method A Step 1

2-(trimethylacetylamino)-6-bromopyridine: Trimethylacetyl chloride (180.9 g, 1.500 mols) was added over 1 h to a mixture of 2-amino-6-bromo-pyridine (264.7 g, 1.530 mols), triethylamine (166.7 g, 1.650 mols) and toluene (1 L, KF=2 mg moisture/L) maintaining the temperature below 50° C. The mixture was aged at 25° C. for 42 h. A solution of 1M aqueous HCl (500 mL) was added and the biphasic mixture was filtered (after agitation for 5 min) through a pad of solka floc (10 g) which was washed with toluene (50 mL). The organic phase was separated from the filtrates and was washed with 1M aqueous HCl (2×500 mL), 2% aqueous NaCl (500 mL) and a mixture of saturated aqueous NaCl (250 mL) and saturated aqueous $NaHCO_3$ (25 mL). The organic phase was dried over $MgSO_4$ (10 g), filtered and evaporated to dryness to provide 380.7 g of crude title compound, which was diluted with toluene to give 1480.8 g of crude solution.

Step 2

2-(trimethylacetylamino)-6-formylpyridine: A solution of 2.1 M isopropylmagnesium chloride in tetrahydrofuran (555.3 g, 1.20 mol) was added over 1.5 hours to the crude solution of 2-(trimethylacetylamino)-6-bromopyridine in toluene (501.2 g of crude solution from previous step, 0.500 mol) maintaining the temperature below 3° C. The resulting mixture was aged at 5° C. for 24 hours. Dimethylformamide (112.3 g, 1.54 mol) was added over 20 min maintaining the temperature at 11–15° C. After 15 min, the solution was transferred into 1 L of 10% aqueous acetic acid and the biphasic mixture stirred for 30 min. The organic phase was separated and combined with 500 mL of 20 wt % aqueous sodium hydrogen sulfite. The biphasic mixture was stirred vigorously for 45 min. The aqueous layer was separated and treated with 500 mL of 20 wt % aqueous $Na_2CO_3$, then extracted with ethyl acetate (2×500 mL). The combined organic layers were concentrated to approximately 400 mL at 50° C., 600 mmHg. The concentrate was dried over 8 g of $MgSO_4$ and filtered to give 363.7 g of yellow solution (25.65 wt % title aldehyde, 93.28 assay g).

$^1$H NMR (400 MHz, $CDCl_3$)δ9.88 (s, 1H), 8.47 (d, J=8.4, 1 H), 8.14 (s, 1 H), 7.85 (t, J=7.7, 1 H), 7.64 (d, J=7.3, 1 H), 1.33 (s, 9 H); $^{13}$C NMR (100 MHz, $CDCl_3$)δ192.3, 177.3, 152.0, 150.6, 139.2, 118.4, 118.2, 39.8, 27.3.

Step 3

2-(trimethylacetylamino)-6-[(4-acetylamino)-1-piperidinyl)-methyl]pyridine

Method A: To a stirred solution of 2-(trimethylacetylamino)-6-formylpyridine (3.40 g, 16.5 mmol) in 34 mL of dimethylformamide was added N-(4-piperidinyl)acetamide acetic acid salt (Reference Example 1, 3.66 g, 18.1 mmol). Sodium triacetoxyborohydride (5.14 g, 23.0 mmol) was added in 5 portions to the above homogenous solution over a period of 2 h at room temperature. The reaction mixture was stirred for 2 h at this temperature. At this time, 35 mL of cold-water was added, and washed with 50 mL of isopropyl acetate. After phase separation, the resulting aqueous layer was adjust to pH ~8 with 17 mL of 1N NaOH/40 mL of sat. $NaHCO_3$, and sodium chloride (20 g) was added thereto. The resultant solution was extracted with ethyl acetate 3 times (60 mL each), and the organic layers were combined and concentrated to dryness to give 3.8 g of the desired compound as a solid. Recrystallization of the resulting bis-amide from ethyl acetate-hexane (30 mL:90 mL) gave a white solid.

Method B: Into a 100 L, 4-neck round bottom flask was charged 8.93 kg of 2-(trimethylacetylamino)-6-formylpyridine solution (contains 2.17 kg of the aldehyde, 10.52 mol) in acetonitrile (prepared by solvent-switch from the ethyl acetate solution). The final volume of the acetonitrile solution was adjusted to 50 L by concentration at reduced pressure (KF<150 mg/mL). N-(4-piperidinyl) acetamide acetic acid salt (2.55 Kg, 14.58 mol) was charged with good stirring, and the solution was cooled to 18° C. (internal temp). Sodium triacetoxyborohydride (STAB, 3.25 Kg, 14.58 mol) was charged using a solid addition apparatus in 4 portions to the above heterogenous mixture over a period of 2 h. After completion of STAB addition, the reaction mixture was further stirred for 2 h at room temperature, cooled to 12° C. with an ice-water bath, and then 12.5 L of water was added through a dropping funnel over 10 min (internal temp: below 23° C.). After 20 min, 12.5 L of 2N NaOH was charged over 10 min. The reaction mixture was stirred for an additional 20 min and then the phases were separated. The aqueous layer was back-extracted with 23 L of isopropyl acetate, and the organic layer was combined with the previous acetonitrile layer. The resulting solution was treated sequentially with 4.88 L of 5 N NaOH and 22 L of 13% NaCl solution, stirred for 5 min, and the phases were separated. The organic layer was batch-concentrated at 45° C. at 23" Hg, and solvent switched to isopropyl acetate (10 L of additional isopropyl acetate was used for azeotrope). The final volume of isopropyl acetate solution was adjusted to 21.7 L for the crystallization. Next, 43.4 L of heptane was added with good stirring over a period of 1.5 h at room temperature. The resulting slurry was stirred for 3 h, and filtered over a filtering-pot. After washing the cake with a combined solution of isopropyl acetate/heptane solution (2.2 L/4.4 L), white crystalline solid was dried under reduced pressure under nitrogen tent for 3 h. This material was further dried in vacuum-oven under nitrogen sweeping for 16 h, affording 3.17 kg of the desired product.

Step 4

2-amino-6-[(4-aminopiperidin-1-yl)methyl]pyridine trihydrochloride salt

Method A: To a stirred solution of 2-(trimethylacetylamino)-6-[(4-acetylamino-1-piperidinyl) methyl]pyridine (1.0 g, 3.0 mmol) in methanol (10 mL) was added 6N HCl (10 mL) at room temperature. The resulting mixture was heated to reflux for 16 h. The reaction mixture was cooled to room temperature and concentrated on a rotary evaporator. After azeotropic distillation to remove water with 1-propanol twice (20 mL each), the resulting solid was treated with 10 mL of methanol. After being stirred for 1h in methanol, 10 mL of methyl t-butyl ether was added slowly and stirred for additional 1 h at room temperature. Filtration followed by drying of the crystalline solid gave 0.81 g (86% yield) of the title compound with 99.4 A % purity.

Method B: A 22 L, 4 neck round bottom flask equipped with reflux condenser was charged with 4.2 L of methanol and 1 Kg of 2-(trimethylacetylamino)-6-[(4-acetylamino-1-piperidinyl)methyl]pyridine. Then, 2.2 L of aq. 9N HCl solution was introduced slowly at room temperature over 30 min (internal temp was raised to 40° C.). The resulting solution was heated to reflux and stirred for 30 h at 72° C. (internal temperature). The reaction mixture was cooled to room temperature, and added into 30 L of isopropanol at room temperature over a period of 2 h with efficient stirring. After aging for 2 h at room temperature, followed by another 2 h at 0 to 2° C., the slurry was filtered over a filter pot under nitrogen. The resulting filter-cake was rinsed with 6 L of methanol/isoproanol (1:6) and dried under a stream of nitrogen under reduced pressure for overnight. Further drying in vacuum oven at 32° C. with flush of nitrogen (24" mmHg) for 3 day (until reaching the constant weight) provided 0.86 Kg of the desired product as a non-hygroscopic crystalline solid.

EXAMPLE 2

Preparation of 2-amino-6-[(4-aminopiperidin-1-yl) methyl]pyridine trihydrochloride salt—Method B Step 1

2-(trimethylacetylamino)-6-[(4-t-butoxycarbonylamino-1-piperidinyl)methyl]pyridine formic acid salt: To a stirred solution of 2-(trimethylacetylamino)-6-formylpyridine (3.00 g, 14.6 mmol) in 1:1 ethyl acetatetetrahydrofuran (24 mL) was added 4-amino-N-Boc-piperidine (reference example 2, 3.38 g, 18.2 mmol) and acetic acid (1.16 mL, 20.3 mmol) at 15° C. Then, sodium triacetoxyborohydride (4.50 g, 20.1 mmol) was added in 4 portions to the above homogenous solution over a period of 1.5 h at room temperature. Then, additional of tetrahydrofuran (6 mL) was added. After stirred for 1 h at room temperature, water (3 mL) was added maintaining the temperature below 15° C. with an ice-water bath. The reaction mixture was stirred for 10 min (after evolution of hydrogen) and 1N NaOH (22 mL) was added at this temperature. The mixture was extracted with ethyl acetate (3×40 mL) and the ethyl acetate extract washed with brine (40 mL). Then, the resulting solution was concentrated under reduced pressure and re-dissolved in ethyl acetate (40 mL) and treated with formic acid (1 mL). Then, the solvent was switched with methyl t-butyl ether (30 mL) and hexane (50 mL) was added dropwise. After stirring for 1.5 h at room temperature, the solvent was decanted and the residual formate salt of reductive amination product was dried to give 4.9 g (90%) as a sticky material.

Step 2

2-amino-6-[(4-amino-1-piperidinyl)methyl ]pyridine trihydrochloride salt: To a stirred solution of 2-(trimethylacetylamino)-6-[(4-t-butoxycarbonylamino-1-piperidinyl)methyl]pyridine formic acid salt (0.74 g, 3.0 mmol) in methanol (6 mL) was added 6 N HCl (2 mL) at room temperature. The resulting mixture was heated to reflux for 10 h. Then, the reaction was cooled to room temperature and concentrated under rotary evaporator. After azeotropic removal of water with 1-propanol twice (20 mL each), the resulting solid was treated with methanol (5 mL). After being stirred for 1 h in methanol, ethanol (12 mL) was added slowly and stirred for additional 1 h. After filtration, drying of the resulting crystalline solid gave the desired title compound (491 mg, 80% yield, 98 A % purity).

EXAMPLE 3

(2R)-N-[1-(6-aminopyridin-2-ylmethyl)piperidin-4-yl]-2-[(1R)-3,3-difluorocyclopentyl]-2-hydroxy-2-phenylacetamide In a separation vessel, (2R)-2-[(1R)-3,3-difluorocyclopentyl]-2-hydroxy-2-phenylacetic acid dicyclohexylamine salt (Reference Example 3, 10.0 g, 22.8 mmol, 1 eq.) was mixed with 1.02 N NaOH (65 mL, 2.91 eq, Aldrich), n-heptane (50 mL). The two layers were separated. The bottom aqueous layer was re-extracted with n-heptane (50 mL) and the aqueous layer was mixed with acetonitrile (65 mL), hydroxybenzotriazole hydrate (3.06 g, 22.8 mmol, 1 eq), 2-amino-6-[(4-aminopiperidin-1-yl)methyl]pyridine trihydrochloride (7.56 g, 23.9 mmol, 1.05 eq).

After all of the solid was dissolved, 1-ethyl-3-(3-dimethylaminopropyl)carbodiimide (5.24 g, 27.36 mmol, 1.2 eq) was added. The resulting solution was homogenous. The pH of the solution was about 6. The batch was aged at 35° C. for 4 hrs, then cooled to ≦15° C. and charged with 14 mL 5 N NaOH (3 eq), 65 mL methyl t-butyl ether, and the two layers cut. The quench was exothermic, cold water bath was used to keep the batch ≦30° C.

The organic layer was washed with 2×40 mL 1 N NaOH and separated. To the organic layer was added 34 mL 2N HCl (3 eq) and the layers cut. To the organic layer was added 30 mL heptane and 11 mL 2N HCl (1 eq) and layers cut again. The top organic layer was discarded and the aqueous layers were combined. The combined aqueous layers were mixed with 65 mL methyl t-butyl ether, cooled to ≦15° C., and then 20 mL 5 N NaOH. The pH of the aqueous layer should be ≧11 (adjust with 5 N NaOH if necessary). Cold water bath was used to cool the batch to room temperature The two layers were cut and the top organic layer washed with 40 mL brine.

The organic layer was concentrated on a rotavap to about 40 g, flushed with 2×100 mL isopropyl acetate until KF≦400 mcg/ml when the batch is at about 140 g (~150 mL). At this point, some solid may be precipitated. To this was then added more isopropyl acetate (KF≦150 mcg/ml) until total volume is 260 mL (230 g). To the resultant hazy solution was then added 0.5 g Darco G-60 charcoal and the mixture stirred for 1 hr. The mixture was then filtered through a pad of celite (half inch thick) to get a clear solution. The celite cake was washed with 10 ml isopropyl acetate. The filtrate was then concentrated in vacuum to about 90 ml (80 ml isopropyl acetate +9 g product) or 80 g.

The resulting slurry was heated to 70° C. to dissolve all of the solid, then n-heptane was added while keeping the temperature of the batch at 70° C. After 20 ml n-heptane was added, the batch was seeded and aged for 30 min so some crystals were formed. The rest of the n-heptane (total of 160 ml, 2× of the isopropyl acetate volume) was added over 2 hours. The batch was aged at 70° C. for 1 hour and then allowed to cool to room temperature (22° C.) over 1.5 hrs and aged overnight at ambient temperature. The solid product was collected by filtration and cake washed with 2×25 ml 2/1 n-heptane/isopropyl acetate and then 25 ml n-heptane. The product was dried in a vacuum oven under nitrogen sweep at 45° C. overnight to wt 8.0–8.2 g.

Reference Example 1

Preparation of N-(4-piperidinyl)acetamide acetic acid salt

To a stirred solution of 4-amino-1-benzylpiperidine (100 g, 525.5 mmol) in 1L 2-propanol was added acetic anhydride (59 g) dropwise at 0° C. over 20 min. The reaction mixture was aged at room temperature overnight and carried on to the next step for hydrogenation.

The hydrogenation was done at 45 psi, room temperature with 22 g of 10% Pd/C (50% wet) and stopped when theoretical amount of $H_2$ was consumed (6 h). The crude solution was filtered over 300 g Solka-floc (pre-washed with 200 mL of 2-propanol) under $N_2$, rinsed with 2×100 mL 2-propanol, then the filtrate was concentrated to about 300 mL of solution. Heptane (700 mL) was added through dropping funnel with good stirring to obtain white precipitates which were aged at 0° C. for 3 hours, then filtered under $N_2$, washed with 3×150 mL heptane, dried in a vacuum oven overnight to give 102 g of the title compound as a white crystalline solid.

Reference Example 2

Preparation of 4-(t-butoxycarbonylamino)piperidine

A solution of di-t-butyl dicarbonate (120.4 g, 0.552 mol) in tetrahydrofuran (100 mL) was added to a solution of 4-amino-1-benzylpiperidine (100 g, 0.526 mol) in tetrahydrofuran (600 mL) over 15 min maintaining the temperature below 16° C. The mixture was aged for 2.5 h at 19° C. and concentrated to half its volume in vacuo. The mixture was partitioned between ethyl acetate (700 mL) and water (500 mL). The organic phase was washed with water (500 mL)

and the combined aqueous washes were back extracted with ethyl acetate (500 mL). The combined organic phases were washed with brine (400 mL) dried over $Na_2SO_4$ and solvent switched to ethanol (2600 mL) final volume.

The crude solution containing 130 g of 4-(t-butoxycarbonylamino)-1-benzylpiperidine (0.448 mol) was hydrogenated at 45 psi, room temperature in the presence of 10% Pd/C (52 g, 50% wet) and stopped when theoretical amount of $H_2$ was consumed (23.5 h, TLC). The mixture was filtered from the catalyst and the cake was washed with ethanol (500 mL). The filtrate was concentrated to about 100 mL, redissolved in ethanol and reconcentrated. The mixture was solvent switched to heptane (200 mL final volume) and cooled to 2° C. The slurry was filtered and the solid was washed with heptane (200 mL). The solid was dried in a vacuum oven overnight to give 84 g of the title compound as a white crystalline solid.

Reference Example 3

Preparation of (2R)-[(1R)-3,3-difluorocyclopentyl]-2-hydroxy-2-phenylacetic acid dicyclohexylamine salt Step 1

(2R,5R)-2-(tert-Butyl)-5-[(1R)-3,3-difluorocyclopentyl]-5-phenyl-1,3-dioxolan-4-one Deoxofluor™ (10.5 kg) was dissolved in toluene (28 L) in a Teflon or Hasterlloy reactor and chilled to 5° C. Boron-trifluoride etherate (450 mL) was dissolved in 2 L of toluene and added to the Deoxofluor solution. The mixture was aged for 2 hr at 5° C. (2R,5R)-2-(tert-butyl)-5-[(1R)-3-oxocyclopentyl]-5-phenyl-1,3-dioxolan-4-one (10 kg) was dissolved in toluene (30 L) and the resulting solution was added to the previous mixture after the 2 hr age. The resulting solution was heated at 55° C. for 30 to 40 hr. The HPLC assay indicated <2 area % starting material remained. The aged mixture was cooled to room temperature and added to a pre-cooled ( 5° C.) mixture of NaOH (2 $\underline{N}$, 200 L) and toluene (200 L), maintaining the internal temperature <18° C. After aging for 30 min the aqueous layer was removed and the organic layer was washed with NaOH (2 $\underline{N}$, 100 L). The organic layer from the above reaction was washed with DI water (100 L), then evaporated and solvent switched to a MeOH solution of a volume of 110 L (100 L MeOH).

Step 2

(2R)-[( 1R)-3,3-difluorocyclopentyl]-2-hydroxy-2-phenylacetic acid dicyclohexylamine salt The methanol solution of (2R,5R)-2-(tert-butyl)-5-[(1R)-3,3-difluorocyclopentyl]-5-phenyl-1,3-dioxolan-4-one from Step 1 was treated with LiOH (2N, 7.5 L, 15 moles, 4.5 eq.) and the mixture was heated to 40° C. for 20 hours. Upon completion of the reaction, the mixture was cooled to 30° C., transferred to a 100 L extractor and washed with hexane (20 L). The layers were separated and the aqueous layer cooled to 7° C. and treated with isopropyl acetate (25 L) and 3 N HCl to pH 2.5 to 3.

The layers were separated, the organic layer washed with water and then the layers were separated again. The organic layer was treated with Darco G-60 activated carbon (500 g) and the mixture was stirred for 45 minutes at ambient temperature. The slurry was filtered through solka floc and the carbon cake was washed with isopropyl acetate (8 L).

The organic solution was solvent-switched to methyl-ethyl ketone (24 L), warmed to 60° C. and dicyclohexylamine (606 mL, 3.04 mole,1 eq.) was added in one portion. The resulting solution was aged for 1.5 h at 55–60° C. Crystallization initiated spontaneously, and the slurry was cooled slowly to ambient temperature where it was aged for 4 h. The product was filtered and the filter cake was washed with methyl-ethyl ketone (5 L). The cake was dried in vacuo with a $N_2$ sweep to afford 1.08 kg of an off white solid. Further purification, if needed, can be achieved by dissolving the solid in MeOH (12 L) at 55° C. and cooling the solution to 40° C. to induce crystallization. The slurry of the salt in MeOH was cooled further to 30° C. and water (18 L) was added over 1 h. The slurry was then cooled to 20° C. and aged for 1.5 h. The product was filtered and the filter cake was washed with 1:2 $MeOH:H_2O$(1.5 L). The solid was dried under vacuum with $N_2$ sweep at 25° C. to afford 928 g of the title product salt.

What is claimed is:

1. A process for the preparation of 2-amino-6-[(4-aminopiperidin-1-yl)methyl]pyridine of formula (I) acid addition salt:

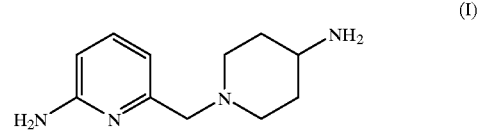

which comprises the steps of:

a) reacting 2-amino-6-bromopyridine with an acylating agent derived from trimethylacetic acid, in the presence of a base, to provide 2-(trimethyl-acetylamino)-6-bromopyridine;

b) treating 2-(trimethylacetylamino)-6-bromopyridine with a metallating agent followed by a formamide of the formula $HC(O)NR^1R^2$ wherein $R^1$ and $R^2$ are independently selected from $C_{1-5}$alkyl and phenyl, to provide 2-(trimethylacetyl)-6-formylpyridine;

c) reacting 2-(trimethylacetylamino)-6-formylpyridine with 4-protected aminopiperidine or an acid addition salt thereof, in the presence of a reducing agent, to provide 2-(trimethylacetylamino)-6-[(4-protected aminopiperidin-1-yl)methyl]pyridine;

d) treating 2-(trimethylacetylamino)-6-[(4-protected amino-piperidin-1-yl)methyl]pyridine with a mineral acid or a strong organic acid; and e) isolating the acid addition salt of 2-amino-6-[(4-amino-piperidin-1-yl)methyl]pyridine.

2. A process of claim 1 wherein said acid addition salt is the trihydrochloride salt, and the mineral acid is hydrochloric acid.

3. A process of claim 2 wherein in step a) the acylating agent is trimethylacetyl chloride; in step b) the metallating agent is isopropylmagnesium chloride and the formamide is dimethylformamide; and in step c) the 4-protected aminopiperidine is 4-(acetylamino)piperidine acetate or 4-(t-butoxycarbonylamino)-piperidine.

4. 2-Amino-6-[(4-aminopiperidin-1-yl)methyl]pyridine trihydrochloride salt prepared by the processes of claim 3.

5. A process for the preparation of a compound of formula (A) or a pharmaceutically acceptable salt thereof:

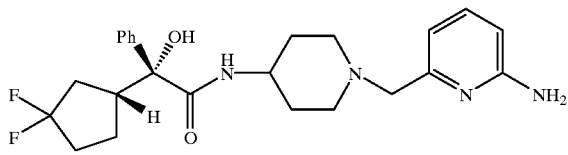

(A)

which comprises the steps of:
a) reacting 2-amino-6-bromopyridine with an acylating agent derived from trimethylacetic acid, in the presence of a base, to provide 2-(trimethyl-acetylamino)-6-bromopyridine;
b) treating 2-(trimethylacetylamino)-6-bromopyridine with a metallating agent followed by a formamide of the formula HC(O)NR¹R² wherein $R^1$ and $R^2$ are independently selected from $C_{1-5}$alkyl and phenyl, to provide 2-(trimethylacetyl)-6-formylpyridine;
c) reacting 2-(trimethylacetylamino)-6-formylpyridine with 4-protected aminopiperidine or an acid addition salt thereof, in the presence of a reducing agent, to provide 2-(trimethylacetylamino)-6-[(4-protected aminopiperidin-1-yl)methyl]pyridine;
d) treating 2-(trimethylacetylamino)-6-[(4-protected amino-piperidin-1-yl)methyl]pyridine with a mineral acid or a strong organic acid;
e) isolating the acid addition salt of 2-amino-6-[(4-amino-piperidin-1-yl)methyl]pyridine;
f) reacting the product of step b) with an acid of the formula

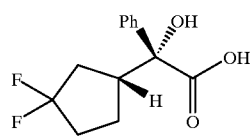

or a acylating agent thereof; and
g) optionally converting the product of step c) into a corresponding pharmaceutically acceptable salt.

6. A process of claim 5 wherein said acid addition salt is the trihydrochloride salt, and the mineral acid is hydrochloric acid.

7. A process of claim 6 wherein in step a) the acylating agent is trimethylacetyl chloride; in step b) the metallating agent is isopropylmagnesium chloride and the formamide is dimethylformamide; and in step c) the 4-protected aminopiperidine is 4-(acetylamino)piperidine acetate or 4-(t-butoxycarbonylamino)-piperidine.

8. The compound 2-(trimethylacetylamino)-6-formylpyridine.

9. A compound selected from 2-(trimethylacetylamino)-6-[(4-acetylaminopiperidin-1-yl)methyl]pyridine and 2-(trimethylacetylamino)-6-[(4-(t-butoxycarbonylamino)piperidin-1-yl)methyl]pyridine.

* * * * *